United States Patent
Peters et al.

(10) Patent No.: US 8,580,865 B2
(45) Date of Patent: Nov. 12, 2013

(54) PHASE-AND SEDIMENTATION-STABLE, PLASTICALLY DEFORMABLE PREPARATION WITH INTRINSIC PORE FORMING, INTENDED FOR EXAMPLE FOR FILLING BONE DEFECTS OR FOR USE AS BONE SUBSTITUTE MATERIAL, AND METHOD OF PRODUCING IT

(75) Inventors: Fabian Peters, Frankfurt am Main (DE); Christiane Hoffmann, Frankfurt am Main (DE); Kathleen Hasanovic, Frankfurt am Main (DE)

(73) Assignee: Curasan AG, Kleinostheim (DE)

( * ) Notice: Subject to any disclaimer, the term of this patent is extended or adjusted under 35 U.S.C. 154(b) by 77 days.

(21) Appl. No.: 12/310,770

(22) PCT Filed: Aug. 30, 2007

(86) PCT No.: PCT/DE2007/001561
§ 371 (c)(1),
(2), (4) Date: Mar. 5, 2009

(87) PCT Pub. No.: WO2008/028466
PCT Pub. Date: Mar. 13, 2008

(65) Prior Publication Data
US 2009/0254194 A1  Oct. 8, 2009

(30) Foreign Application Priority Data
Sep. 6, 2006 (DE) .......................... 10 2006 042 142

(51) Int. Cl.
*A61F 2/28* (2006.01)
*C08K 3/32* (2006.01)

(52) U.S. Cl.
USPC ......... 523/115; 523/116; 524/414; 623/23.62

(58) Field of Classification Search
USPC ................ 523/115, 116; 524/414; 623/23.62
See application file for complete search history.

(56) References Cited

U.S. PATENT DOCUMENTS

| | | | |
|---|---|---|---|
| 4,780,450 A | 10/1988 | Sauk et al. | |
| 5,204,382 A | 4/1993 | Wallace et al. | |
| 5,258,028 A | 11/1993 | Ersek et al. | |
| 5,352,715 A | 10/1994 | Wallace et al. | |
| 5,840,290 A | 11/1998 | Hench et al. | |
| 5,922,025 A | 7/1999 | Hubbard | |
| 6,117,444 A * | 9/2000 | Orgill et al. | 424/426 |
| 6,417,247 B1 * | 7/2002 | Armstrong et al. | 523/115 |
| 6,437,018 B1 | 8/2002 | Gertzman et al. | |
| 6,793,725 B2 * | 9/2004 | Chow et al. | 106/35 |
| 6,811,776 B2 * | 11/2004 | Kale et al. | 424/93.7 |
| 6,903,146 B2 | 6/2005 | Matsushima et al. | |
| 7,128,967 B2 * | 10/2006 | Hiraide et al. | 428/323 |
| 2002/0169506 A1 | 11/2002 | Matsushima et al. | |
| 2003/0055512 A1 | 3/2003 | Genin et al. | |
| 2005/0124720 A1 | 6/2005 | Rizzoli et al. | |
| 2006/0110357 A1 | 5/2006 | Materna et al. | |
| 2006/0263443 A1 * | 11/2006 | Chow et al. | 424/603 |
| 2007/0016163 A1 * | 1/2007 | Santini et al. | 604/500 |
| 2007/0128245 A1 * | 6/2007 | Rosenberg et al. | 424/423 |

FOREIGN PATENT DOCUMENTS

| | | |
|---|---|---|
| DE | 102 19 765 | 11/2002 |
| DE | 10 2006 042 | 3/2008 |
| EP | 0 416 398 | 3/1991 |
| EP | 1 142 595 | 10/2001 |
| EP | 1 475 109 | 11/2004 |
| EP | 1 477 176 | 11/2004 |
| EP | 1 772 154 | 4/2007 |
| FR | 2 805 747 | 9/2001 |
| FR | 2 852 249 | 9/2004 |
| GB | 2 377 642 | 1/2003 |
| JP | 6-506862 | 8/1994 |
| JP | 7-504106 | 5/1995 |
| WO | WO-95/21634 | 8/1995 |
| WO | WO-97/45070 | 12/1997 |
| WO | WO-00/07639 | 2/2000 |

(Continued)

OTHER PUBLICATIONS

F. Peters, et al., "Functional Materials for Bone Regeneration from Beta-Tricalcium Phosphate", Mat.-wiss. u. Werkstofftech, 2004, 35, No. 4, pp. 203-207.

(Continued)

*Primary Examiner* — Tae H Yoon
(74) *Attorney, Agent, or Firm* — Jordan and Hamburg LLP (57) ABSTRACT

The invention relates to a phase and sedimentation-stable, plastically deformable preparation with intrinsic pore formation that can be used for instance for filling bone defects and for augmentation, and also relates to a method for producing same. The object of the invention, to provide a phase and sedimentation-stable, plastically deformable implant material with intrinsic pore formation, that is not complex to create, and that can be inserted into a bone defect by injection or alternatively can be applied to/fitted in a bone defect as a kneadable mass, is attained in that a plastically deformable preparation for bone construction/replacement based on ceramic suspension includes a particulate, porous component that is not easily soluble in water and at least one liquid, wax-like, or gel component that is dissolved in water or alcohol, the component that is not easily soluble in water being 60-98% by weight and the composition dissolved in water or alcohol being 1-30% by weight, the particles of the particulate component having a diameter in a size range that is essentially greater than a phagocytabler particle and smaller than the passage diameter of standard injection cannulas and the portion of the dissolved component in the water or alcohol being 0.1-3% by weight.

31 Claims, 4 Drawing Sheets

(56) References Cited

FOREIGN PATENT DOCUMENTS

| WO | WO-00/45867 | 8/2000 |
| WO | WO-01/41821 | 6/2001 |
| WO | WO-01/41824 | 6/2001 |
| WO | WO-02/058755 | 8/2002 |
| WO | WO-03/028779 | 4/2003 |
| WO | WO-03/035124 | 5/2003 |
| WO | WO-03/063686 | 8/2003 |
| WO | WO-03/082365 | 10/2003 |
| WO | WO-2004/011053 | 2/2004 |

OTHER PUBLICATIONS

R. Murugan, et al., "Bioresorbable composite bone paste using polysaccharide based nano hydroxyapatite", Biomaterials 25 (2004), pp. 3829-3835.

* cited by examiner

PHASE-AND SEDIMENTATION-STABLE, PLASTICALLY DEFORMABLE PREPARATION WITH INTRINSIC PORE FORMING, INTENDED FOR EXAMPLE FOR FILLING BONE DEFECTS OR FOR USE AS BONE SUBSTITUTE MATERIAL, AND METHOD OF PRODUCING IT

This patent application is a national stage filing under 35 U.S.C. 371 of International Application No. PCT/DE2007/001561, filed on Aug. 30, 2007, which claims foreign priority benefits to German Patent Application No. 10 2006 042 142.6, filed on Sep. 6, 2006. These applications are incorporated herein by reference in their entireties.

BACKGROUND OF THE INVENTION

The invention relates to a phase and sedimentation-stable, plastically deformable preparation (implant material/bone replacement material) with intrinsic pore formation, that can be used for instance for filling bone defects and for augmentation, and also relates to a method for producing same.

Resorbable and non-resorbable implant materials based on calcium phosphates have been known for some time as bone replacement materials for filling bone defects and for augmentation. In addition to shaped bodies and granulates, in particular injectable and kneadable implant materials are of interest.

One method and composition for repairing bones is disclosed in WO 03/063686. The composition is a hydrogel that is formed from hyaluronic acid and that is mixed with animal bone components, bone-like powder, or hydroxyapatite. Likewise, a growth inducing peptide can be a component of the mixture.

A malleable bone composition for filling bone defects is described in EP 1 477 176 A1. This composition can be embodied as a paste or flowable gel and can comprise inter alia bone powder in a hydrogel carrier. In accordance with EP 1 477 176 A1, the powder component can comprise 25 to 35% of the material and can have a particle size of 100-850 µm. The hydrogel carrier can comprise chitosan having a molecular weight of 100,000-300,000 Daltons and comprising 1-4.5% of the material.

Known from U.S. Pat. No. 5,258,028 are injectable microimplants that comprise a hydrogel made of polyvinylpyrrolidone and a plastic material made of polydimethylsiloxane. Alternative to this polymer, particles made of calcium salts, such as hydroxyapatite, biocompatible ceramics, or biocompatible metals can also be used. The size of the biologically compatible particles can be between 10 and 3000 micrometers.

U.S. Pat. No. 4,713,076 discloses a coating composition that comprises highly porous spherical particles and a resorbable binder. The particles comprise tricalcium phosphate and the binder comprises gelatins, polyamino acids, or collagen.

U.S. Pat. No. 4,780,450 suggests a composition for bone treatment, the composition containing polycrystalline, particulate calcium phosphate ceramic, acid, phosphorous-containing proteins, and type I collagen. In U.S. Pat. No. 4,780, 450, hydroxyapatite, β-tricalcium phosphate ceramic, or mixtures thereof are listed as calcium phosphate ceramics.

EP 0416 398 A1 also describes paste-like bone replacement material, the materials being formed from an aqueous solution of pullulan, glycol chitin, carboxymethyl chitin and pectin, in which solution calcium phosphate particles are suspended. Hydroxyapatite, fluorapatite, α-tricalcium phosphate, β-tricalcium phosphate, and tetracalcium phosphate are used as calcium phosphates.

US 2002/169506 also describes kneadable fill materials, these materials comprising calcium phosphate granulate and so-called "small chips". These chips are formed from chitin and after contact with water are intended to bind the granules of the calcium phosphate granulate in that they stick together.

WO 03/082365 describes a kneadable and pliable bone replacement mass that comprises a mixture of calcium-containing ceramic particles and a hydrogel or a substance that can swell to form a hydrogel, the ceramic particles being of entirely synthetic origin and the majority of the ceramic particles not being round in shape. The individual ceramic particles have an at least partially cohesive, porous structure. The calcium-containing ceramic particles can comprise dicalcium phosphate dihydrate, dicalcium phosphate, α-TCP, β-TCP, wherein "TCP" means tricalcium phosphate, calcium-deficient hydroxyapatite, hydroxyapatite, carbonate apatite, chlorapatite, whitlockite, tetracalcium phosphate, oxyapatite, calcium pyrophosphate, and octacalcium phosphate. The substances that can swell to form hydrogels can contain polyamino acids, polysaccharides, polylipids, nucleotides, or combinations thereof as components.

Patent application US 2003/055512 discloses an injectable, bioresorbable bone replacement material based on calcium. The material is a mixture of calcium sulfate and a phosphate cement powder that hardens after mixing with water.

A paste for treating bones is known from WO 2004/011053. This paste comprises a carrier gel based on hyaluronic acid and synthetic hydroxyapatite suspended therein or comprises hydroxyapatite prepared from bone material.

"Bioresorbable composite bone paste using polysaccharide based nano hydroxyapatite" (R. Murugan, S. Ramakrishna, *Biomaterials* 2004, 25 3829-3835) describes a paste having nanoparticulate, precipitated hydroxyapatite. Sols made of chitosan, a polysaccharide, are used for binders and matrix for the hydroxyapatite particles.

FR 28 52 249 discloses a bone filling material, especially for use in conjunction with oral implants, comprising a source of phosphate and calcium and a stimulant for stimulating collagen production using osteoblasts, for instance in the form of hydroxyproline-mono or di-palmitate. Cited as calcium phosphate sources are hydroxyapatite, dicalcium phosphate, α-tricalcium phosphate, β-tricalcium phosphate, tetracalcium phosphate, and octacalcium phosphate, which are intended to stimulate collagen formation. The composition can be produced in different forms, inter alia having a viscosity that permits application in a syringe.

The viscosity of the composition is set by means of cohesion promoters that belong to the group of celluloses, amidones, cyclodextrines, alginates, dextransul fates, polyvinylpyrrolidones, or hyaluronic acid. The grain size of the calcium phosphate is less than 100 µm and can be 50, 20, 10, or 5 µm. Combination with platelet rich plasma (PRP) and other growth factors is possible.

WO 03/035124 describes bioactive materials and methods for producing and using same. Disclosed in this publication inter alia is a bioactive composition made of a fibroin suspension and optionally a pore-forming, particulate material. The fibroin suspension can have the form of an occlusion, a gel, a crème, or a paste. The fibroin can derive from the fiber substance of silk threads from the *Bombyx mori* silkworm. The pore-forming, particulate material can be hydroxyapatite, tricalcium phosphate, Korelle, chitosan, or a combination of these materials. Furthermore, the pore-forming, particulate materials can be a composite in which the core can comprise calcium phosphates or glass ceramics and the surrounding shell can comprise one or a plurality of biodegradable polymers such as polylactide, polyglycolide, poly-alpha-hydroxy acids, polyamides, etc.

Known from WO 03/028779 is an injectable osseous defect filler comprising calcium salt particles, an organic binder having an affinity to the calcium salt, cells from the group of stem cells, osteogenic cells, and osteoprogenitor cells, and a pharmaceutically acceptable buffer. In this osseous filler, calcium phosphate particles, such as for instance monetite ($CaHPO_4$), brushite ($CaHPO_4*2H_2O$), calcium pyrophosphate, and also calcium carbonate and combinations thereof are used as calcium salts. The calcium salts can also comprise hydroxyapatite and β-TCP or mixtures thereof. The particle diameter of the calcium salts is in the range of 100 to 600 μm, preferably in the range of 200 to 400 μm. Alginates, dextrans, celluloses and their derivatives, plasma, biogenic binders, hyaluronic acid and combinations thereof are cited as organic binders. Hyaluronic acid, sodium alginate, sodium carboxymethyl cellulose, dextran, fibrin glue, and transglutaminase are preferred. WO 03/028779 states that the best effects are obtained with sodium alginate. In accordance with this publication, the quantities of binder are in the range of 0.5 to 10% by weight, preferably in the range of 3 to 7% by weight. A phosphate buffer (PBS) is used for the buffer. The solid content is in the range of 30 to 70, preferably in the range of 40 to 60% by weight. According to WO 03/028779, pastes having a viscosity of 30,000 to 100,000 centipoise can be easily injected. The needles used have a diameter of 2 to 5 mm and a length of 5 to 20 mm. The information regarding the force necessary for injection is provided as a function of different parameters. Additional growth factors may be present in addition to the cells that colonize on the surface of the calcium phosphate particles.

Known from WO 02/058755 is an injectable porous bone replacement material that can increase its porosity in situ. This material comprises a bone-like compound and a hydrophobic carrier. The bone-like compound can comprise calcium phosphates, potassium phosphate, calcium sulfate, hydroxyapatite, bioactive glasses, and combinations thereof. The hydrophobic substances can comprise proteins, glycoproteins, polyesters, polyanhydrides, polyamines, wax-like biodegradable polymers such as polyglycolid and combinations thereof.

Moreover, in accordance with WO 02/058755, aqueous components and mixtures of a degradable component and the aforesaid bone-like substances can be used. The biodegradable components can comprise polyhydroxypolyesters, albumin, collagen, proteins, polysaccharides, glycoproteins, and combinations thereof. A gas forming component, for instance hydrogen peroxide and/or peroxidase, is suggested for producing porosity.

WO 01/41821 describes an injectable, self-setting mixture that enables formation of hardened biomaterials with broad variations in properties. This mixture comprises a water-based liquid component, at least one cationic polymer, and a monophosphate salt having a pH in the range of 6.5 to 7.4. According to WO 01/41821, the aqueous phase has endothermal gel-forming properties. The second component of the mixture comprises at least two calcium phosphates made of apatites, octacalcium phosphates, amorphous calcium phosphates, tetracalcium phosphates, tricalcium phosphates, dicalcium phosphates, and monocalcium phosphates. The cationic polymer is contained in the first component at 0.1-5.0% by weight and can comprise polysaccharides, polypeptides or synthetic polymers, chitin, or chitosan. The monophosphate salt can constitute sodium potassium phosphates, magnesium phosphates, manganese phosphates, or iron phosphates with different stoichiometry. Mentioned as water-soluble polymers are various modified celluloses, polyethylene glycol, polyvinyl alcohol, organic polyols, glycol oligomers, sugar, and glycerol. The mixture can furthermore contain growth factors.

EP 1 475 109 A1 discloses a formulation for injectable application of osteogenic proteins comprising a pharmaceutically acceptable admixture of the osteogenic protein and a hemostatic gelatin foam paste. This formulation can also contain tricalcium phosphate. The osteogenic proteins can derive from the BMP (bone morphogenetic protein) family, preferably BMP-2 and OP-1. The TCP (tricalcium phosphate) particles are microporous and have a particle size of 45-125 μm, which can be injected through an 18-gauge needle (equivalent of 1.2 mm diameter and 40 mm length). Moreover, this publication also describes alginates or celluloses as agents for controlled release of the proteins.

Known from WO 01/41824 is a hydraulic brushite cement that is stabilized with magnesium salts. The brushite cement can be produced from an basic calcium phosphate, a second component comprising an acid calcium phosphate, a third component comprising water, and a fourth component, for controlling the setting reaction, comprising a magnesium salt. In accordance with WO 01/41824, the basic calcium phosphates can derive from the class of tricalcium phosphates and apatites. The acid phosphate components can comprise monocalcium phosphates. The fourth component, contained as from 0.001 to 60% by weight, can derive from various magnesium phosphates and magnesium salts of organic compounds.

The liquid components can also contain sulfuric acid or phosphoric acid. In accordance with WO 01/41824, additives can be used for controlling the flow properties of the cements. These can comprise polysaccharides, preferably hyaluronic acid and its salts, dextran, alginate, hydroxypropylmethyl cellulose, chitosan, or xanthan. The cement can contain granules with diameters ranging from 100 μm to 500 μm, preferably ranging from 200 to 350 μm. The granules can comprise calcium phosphate or gypsum. The set cement mixture can have a Ca:P ratio of 1.00 to 1.67.

WO 00/07639 discloses bone precursor compositions and methods for producing same. These compositions can contain injectable calcium cements made of monocalcium phosphate monohydrate and β-TCP ("TCP" meaning tricalcium phosphate) and also calcium pyrophosphate and calcium sulfate. These calcium cements can have granular shapes ranging from 1 to 500 μm. Collagens, methylcellulose, biopolymers, or other pharmaceutically acceptable substances may be contained for controlling viscosity. In addition, CAPS, triethanolamine, TES, tricine, HEPES, glycine, PBS, bis tris propane, TAPS, AMP, and TRIS can be used to neutralize the pH of the bone precursor substance.

WO 00/45867 discloses a hydraulic cement having a calcium source, water, and a hydrophobic liquid. This mixture constitutes a calcium source and water, which when mixed with one another results in a self-hardening cement paste. A third component comprises a hydrophobic liquid that, washed out in situ, results in a cement having an open macroporosity that permits rapid bone ingrowth. The hydrophobic liquid can derive from the group of fats or oils. The calcium source can derive from the class of calcium phosphates. The Ca:P ratio for the calcium source can be between 1.0 and 1.67. In this regard, the publication cites inter alia monocalcium phosphate monohydrate and anhydrous monocalcium phosphate, dicalcium phosphate, octacalcium phosphate, alpha and beta tricalcium phosphate, tetracalcium phosphate, hydroxyapatite. Polymer additives can be used as additives for controlling the flow properties of the cement. These additives can derive from the group of polysaccharides and can include for instance modified celluloses such as hydroxypropylmethyl cellulose, hydroxyethyl cellulose, and hyaluronic acid. Moreover, an emulsifying agent from the group of surfactants can be used as a stabilizer. Pharmaceutically and physiologically active substances can be added in.

Known from WO 95/21634 is a biomaterial composition and a method for producing same. The composition can contain 40 to 75% by weight β-tricalcium phosphate and hydroxyapatite in a ratio of from 20:80 to 70:30, as well as calcium titanium phosphate ($CaTi_4(PO_4)_6$) and 60 to 25% by weight of a liquid phase, comprising an aqueous solution of a cellulose derivative. Furthermore, the publication also mentions hydroxypropyl methylcellulose.

The size of the granules is 80 to 200 μm. The material is sterile, ready for use, and injectable.

SUMMARY OF THE INVENTION

The disadvantage of many of the aforementioned known mixtures is that they are not homogenous or stabile over an extended period of time. In addition, there is the fact that some mixtures cannot be applied using cannulas because of their nature. In terms of the compositions from the prior art that contain calcium phosphate, there is the problem that over an extended period of time a relatively solid calcium phosphate phase that cannot be kneaded settles out under an aqueous phase, which is particularly disadvantageous for the commercial viability of pre-manufactured mixtures.

The present invention is intended to eliminate the aforesaid deficiencies of the prior art in a simple manner and to provide a phase and sedimentation-stable, plastically deformable implant material with intrinsic pore formation that has a viscous to paste-like consistency, that is not complex to create, and that can be inserted into a bone defect by injection or alternatively can be applied to/fitted in a bone defect as a kneadable mass. It is furthermore the object of the invention to provide a method for producing this material.

The essence of the invention is comprised in that particles are used that have a diameter in a range that is greater than a phagocytable particle (in section 2 "Particle Size and Mechanical Properties", F. Peters, D. Reif publication "Functional Materials for Bone Regeneration from Beta-Tricalcium Phosphate", Mat.-wiss. u. Werkstofftech. 2004, 35 (4), 203-207, states that for biomaterials made of beta-tricalcium phosphate the mean particle size should be in the range of 7-10 μm in order to prevent the phenomenon of phagocytosis) and that is matched to the passage diameter of common injection cannulas and these particles are mixed intimately with a binder substances, stabilizing substances that suppress sedimentation being added simultaneously. The binder substances are organic in nature and can be from the group of alginates, starches, polysaccharides, celluloses, modified celluloses, hyaluronic acids and their salts, gelatins, collagens, polyacrylic acids, aqueous or alcoholic solutions thereof, dextrans, polyethylene glycols, or mixtures thereof.

In accordance with the present invention, it is possible to produce stable, flowable suspensions using anhydrous mixtures of liquid polyethylene glycols and calcium phosphate particles. Likewise, in accordance with the invention, stable suspensions can be produced with aqueous solutions of the aforesaid polysaccharides, alginates, starches, modified celluloses, proteins, and protein mixtures.

Sliding of the ceramic particles relative to one another is effected using the inventive addition of cohesion promoters, particularly advantageously hydrogels, to the composition. At the same time, the inventively added cohesion promoters prevent individual components in the composition from settling (sedimentation) so that the composition is maintained as a homogenous suspension over an extended period of time.

In a bone defect to be filled, the easily soluble hydrogel component acts as an intrinsic pore former. The intermediate spaces between the particles, whose size is a function of particle size and particle size distribution, promote ingrowth of veins and tissue. The more easily soluble hydrogel matrix additionally expands the agglomeration of the particles and at the same acts as a cohesion promoter for insuring injectability. The hydrogel matrix is disposed between the particles. When inserted into the defect, blood coagulates calcium-indicated on the surface of the particle material. The more easily soluble hydrogel component is resorbed within a short period of time; agglomeration of the particles stabilized by the fibrous tissue remains behind. This agglomeration is made of resorbable bioceramic with large interparticulate intermediate spaces now satisfies all of the requirements for a bone replacement material in terms of porosity, freedom from phase shift, and resorbability. The following is understood for the term "not easily soluble". The "not easily soluble" substance dissolves in water at room temperature in a maximum concentration of 100 mg/L.

The inventive addition of substances that are phase-pure (i.e., consisting of a single phase), in particular phase-pure beta-tricalcium phosphate, to the composition effects greater structural stability because no materials having different coefficients of thermal expansion or different solubility cause premature particulate disintegration The inventive composition has particles that have interconnecting pores (micropores ≤0.01-50 μm) so that cells can be fed in vivo, even within the composition/biomaterial. In addition, the liquids (for instance blood or body fluid) dissolve a resorbable/degradable biomaterial (such as for instance beta-tricalcium phosphate) from the inside to the outside so that prompt resorption can accompany bone growth. Due to the interconnecting microporosity of the biomaterial, capillary forces also cause a tamponade-like effect in feeding the defect. Macropores (>50 μm) promote vascularization and provide guides for the growth of newly-formed bone. Pore diameters in the range of 50-100 μm demonstrated good results. Long and winding pores cannot be completely filled with bone if there is no contact with the supply media. Therefore it is necessary to design the large pores so that they are interconnected by small pores. For large blocks of biomaterial, this porosity is attained by adding pore-formers, foaming, or drilling. With granules, the intergranular intermediate spaces satisfy the function of macropores.

Moreover, due to pores being added and due to small particles there is a lower quantity of material per defect volume acting as placeholder in the bone defect. Increased resorption speed results from the lower quantity of material and from the large surface area for smaller particles. The stability of the open structure is optimized by the inventive solution in that no premature decomposition into phagocytable subparticles occurs during the resorption.

It is inventive that porous particles in the size range of 0.1-150 μm, with pore diameters of 0.01-50 μm, can comprise β-tricalcium phosphate, α-tricalcium phosphate, whitlockite, tetracalcium phosphate, octacalcium phosphate, hydroxyapatite, type A carbonate apatite, type B carbonate apatite, calcium-deficient hydroxyapatite, amorphous calcium phosphate, and/or resorbable glass ceramics. The particles can have both a round shape and a polygonally broken shape that is rounded by wear and thermal sintering.

The plastically deformable implant material having particles embodied in this manner can be paste-like or can have a very highly viscous, more kneadable to wax-like form. The paste-like form of the implant material is embodied such that it can be applied to the bone defect in a minimally invasive manner by means of an injection syringe having a straight or angled cannula. The diameters of the particles are optimized for the cannula diameter of an injection cannula. Particle diameters are optimized such that the paste-like material can also be applied using a cannula that is angled up to 60°, measured with respect to the longitudinal axis of the injection syringe.

The inventive particles are not easily soluble in water, are biologically active, and have a polygonally broken rounded shape. This shape attains optimum cohesion of the structural agglomeration of the particles.

It is essential for the invention that it is constructed from a mixture of 60-98% by mass calcium phosphate particles and 1-30% by mass of an aqueous or alcoholic solution of dextran and/or carboxymethyl dextran and/or hyaluronic acid and/or dermatan sulfate, carboxymethyl cellulose and/or oxidized cellulose and/or gelatins and/or mixtures thereof. The use of polysaccharide derivatives, such as for instance carboxymethyl dextran, carboxymethyl hyaluronic acid, and sulfated hyaluronic acid, is also within the sense of the invention. The particular advantage of using hydrophobically modified calcium phosphate particles is that in particular anionic polysaccharides and polysaccharide derivatives, such as hyaluronic acid or carboxymethol dextran, can interact, via their carboxyl groups, with the calcium phosphate surfaces in only a limited manner. This has a positive effect on rheological properties. It is likewise inventive that it is preferably constructed from a mixture of 80-98% by mass calcium phosphate particles, 1-20% by mass anhydrous polyethylene glycol 400, and 1-20% by mass anhydrous polyethylene glycol 600. Polyethylene glycol 400 and polyethylene glycol 600 can also contain oxidation stabilizers, in addition.

The plastically deformable preparation for bone construction/replacement based on ceramic suspensions is inventively in a paste form so that it can be applied using an injection cannula.

The particle shape and particle size of the particulate component that is not easily soluble in water are matched to the diameter of the injection cannula.

The mean particle diameter of the biologically active substance is inventively optimized such that the mixture can be applied using an angled cannula, the angle being up to 60°, preferably 45°, measured with respect to the longitudinal axis of the injection syringe.

The particle size of the ceramic particle to be injected has an upper limit (tilt of the particles just prior to and in the cannula), but it is also limited in terms of the smallest diameter: from various works it is known that large quantities of particles in the range of less than 5 μm-diameter can lead to an excessive reaction to foreign bodies. The particles are absorbed and transported away or metabolized (phagocytosis) by macrophages (large foreign-body-eating cells). This is addressed inter alia in the following publications: S. Shimizu in *Biomed. Res.* 1988, 9 (2), 95 and J. van der Meulen and H. K. Koerten in *J. Biomed. Mater. Res.* 1994, 28, 1455. The consequence can be aseptic excessive reactions to foreign bodies that can trigger inflammation of the surrounding soft tissue. The reduction in pH in the vicinity of the phagocyting macrophages (center of inflammation) leads to the decomposition of additional ceramic into small subparticles that are also phagocyted. Soft tissue can grow into the resultant gaps and thus interfere with successfully correcting the defect.

Therefore, the majority of invention-essential mean particle diameters are larger than the phagocytable size.

The invention-essential mean particle diameters $d_{10}$, $d_{50}$, and $d_{90}$ of the biologically active substance/particles behave as follows for cannula diameter k:

$$K \geq 3/20 * d_{10} + 1/2,\ k \geq 2/25 * d_{50},\ \text{and}\ k \geq 2/25 * d_{90} + 4/5.$$

In addition to particle size, the particle shape also has a characteristic property that is essential to the invention. For attaining a polygonally-broken shape, larger units of the ceramic powder are pressed, sintered (burned), and broken. The broken particles are subjected to a thermal sintering step so that they have a rounded sintered structure. Thus no sharp-edged areas that could lead to irritation of the surrounding soft tissue after implantation can be detected on the particle surface.

The inventive preparation can be in a kneadable form and thus can be more simple to apply and adapt.

When in paste form, the inventive preparation/mixture can be applied using an injection cannula, the mixture having 60-80% by weight, preferably 67-75% by weight β-tricalcium phosphate, 17-37% by weight, preferably 25-35% by weight water, and 0.3-3% by weight, preferably 0.5-1.5% by weight low-viscosity methylcellulose.

A kneadable wax-like inventive preparation can also comprise a mixture of 65-85% by weight, preferably 68-78% by weight β-tricalcium phosphate, 13-32% by weight, preferably 20-30% by weight water, and 0.1-3% by weight, preferably 0.3-1.0% by weight high-viscosity methylcellulose.

Another paste-like form of the inventive preparation that can be applied using an injection cannula can comprise a mixture of 60-80% by weight, preferably 68-76% by weight β-tricalcium phosphate, 15-35% by weight, preferably 25-31% by weight water, and 0.1-3% by weight, preferably 0.2-0.9% by weight low-viscosity methylcellulose, and 0.01-2% by weight, preferably 0.1-0.6% by weight sodium hyaluronate or hyaluronic acid.

One kneadable form of the inventive preparation can comprise a mixture of 60-80% by weight, preferably 65-78% by weight β tricalcium phosphate, 20-35% by weight, preferably 24-30% by weight water, and 0.05-3% by weight, preferably 0.1-0.7% by weight high-viscosity methylcellulose, and 0.05-2% by weight, preferably 0.1-0.5% by weight sodium hyaluronate or hyaluronic acid.

Particularly advantageous is a preparation in the form of a mixture of made of 20-98% by mass calcium phosphate particles, 1-20% by mass anhydrous polyethylene glycol 400, and 1-20% by mass anhydrous polyethylene glycol 600. Moreover, the combinations HS+methocel+dextran; HS+methocel+PEG or HS+methocel+PEG+dextran are particularly advantageous.

The density of the inventive preparation is between 1.3 g/cm$^3$ and 2.1 g/cm$^3$, preferably between 1.6 g/cm$^3$ and 1.9 g/cm$^3$, the water soluble organic binder substance with the particulate biologically active substance forming a porous agglomeration that is dimensionally stable when applied, the easily soluble component in the defect environment being exchanged for fibrous tissue and the porous particle packing thus remaining dimensionally stable and being slowly integrated, vascularized, and resorbed.

It is particularly advantageous when the water-soluble organic binder substance is provided such that it prevents settling of the particulate, biologically active substance in two phases, specifically a dense phase that primarily comprises the particulate substance and an aqueous phase.

It is furthermore particularly advantageous when the hydrogel-forming components that are soluble in water or alcoholic solvents derive from substances from the group of alginates, starches, polysaccharides, celluloses, modified celluloses, hyaluronic acids and their salts, gelatins, collagens, shellac, polyacrylic acids, aqueous or alcoholic solutions thereof, dextranes, polyethylene glycols and their mixtures, and the biologically active substance comprises calcium phosphates and/or sodium-containing and/or potassium-containing and/or calcium-containing and/or silicate-containing acid and/or neutral and/or alkaline bioglasses or mixtures of the aforesaid.

The biologically active substance also particularly advantageously comprises monocalcium phosphate-monohydrate, anhydrous monocalcium phosphate, dicalcium phosphate-dihydrate, anhydrous dicalcium phosphate, β-tricalcium phosphate, α-tricalcium phosphate, tetracalcium phosphate, whitlockite, octacalcium phosphate, hydroxyapatite, oxyapatite, type A carbonate apatite, type B carbonate apatite, calcium-deficient hydroxyapatite, amorphous calcium phosphate, amorphous carbonate-containing calcium phosphate, or mixtures of the aforesaid. The advantage of the inventive paste-like, kneadable, injectable compositions is that the hydrogel forming components that are soluble in water or alcoholic solvents have a property that inhibits crystallization so that recrystallization of the calcium phosphate system or the other possible ceramic components into a different phase by water is suppressed by this stabilizing component.

Moreover, the preparation can contain growth-inducing proteins and thus can effectively promote bone and tissue regeneration. These growth factors can derive from the family of growth factors (GF) or from the bone morphogenetic proteins. Growth factors used are BMP-1 through BMP-12, particularly advantageously BMP-2 and BMP-7, and/or FGF, TGF-β, PDGF, VEGF, IGF, HGF, PTH, and/or mixtures thereof.

Moreover, growth factor mixtures obtained directly from the patient's blood, such as e.g. platelet rich plasma (PRP), can also be contained in the preparation.

The invention is explained in the following using the figures and exemplary embodiments.

DETAILED DESCRIPTION OF THE INVENTION

The inventive preparation based on calcium phosphate suspensions includes:
a) a particulate component that is difficult to dissolve in water, and,
b) at least one liquid or gel component that is soluble in water, so that a paste-like mixture is formed.

The hydrogel component that dissolves more easily acts as an intrinsic pore former in the bone defect.

The intermediate spaces between the particles of the preparation, the size of which is a function of the particle size and the particle size distribution, promote the ingrowth of veins and tissue.

The hydrogel matrix that dissolves more easily also expands the agglomeration of the particles and simultaneously promotes cohesion in order to assure injectability.

Figure 1:
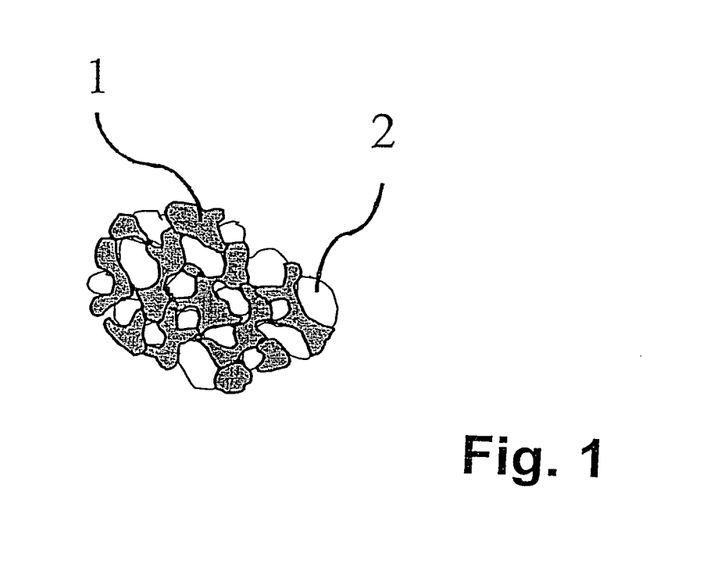
FIG. 1 is an embodiment of the inventive preparation in the form of a particle embedded in a hydrogel matrix.

As FIG. 1 depicts, the hydrogel matrix (1) is located between the particles (2).

Figure 2:
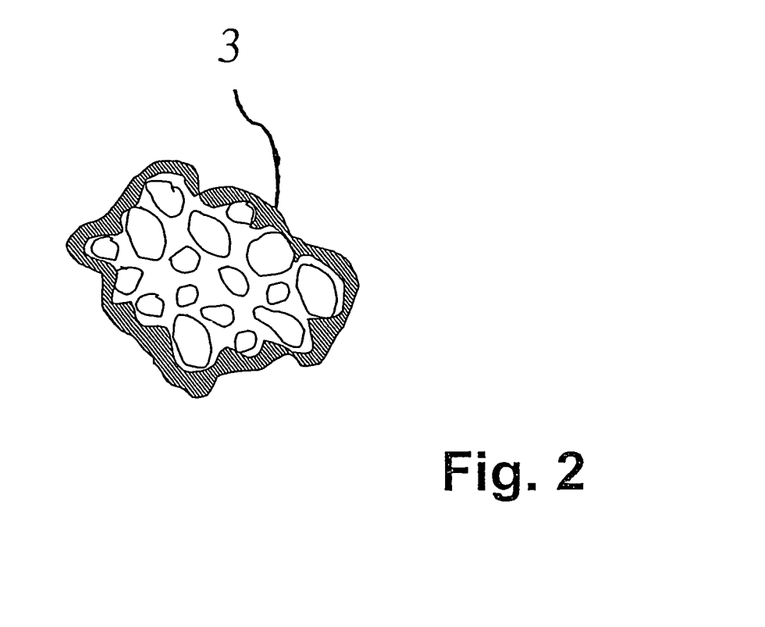
FIG. 2 is the embodiment in accordance with FIG. 1 with coagulated blood on the surface and pores resulting from the released hydrogel matrix.

When the inventive preparation is inserted into the defect, blood (3) coagulates, calcium-indicated, on the surface of the agglomeration of the particles, which is depicted schematically in FIG. 2.

The hydrogel component that dissolves more easily is resorbed within a short period of time so that the particle agglomeration stabilized by fibrous tissue remains. This agglomeration made of resorbable bioceramic having large interparticulate intermediate spaces now satisfies all requirements for a bone replacement material in terms of porosity, freedom from phase shift, and resorbability.

The following is understood for the term not easily soluble. The not easily soluble substance dissolves in water at room temperature in a maximum concentration of 100 mg/L.

In accordance with the invention, the particles in the preparation have a size in the range from 0.1 to 150 μm, pores having a diameter of 0.01-50 μm, and can comprise β-tricalcium phosphate, α-tricalcium phosphate, whitlockite, octacalcium phosphate, hydroxyapatite, type A carbonate apatite, type B carbonate apatite, calcium-deficient hydroxyapatite, amorphous calcium phosphate, and/or resorbable glass ceramics.

The calcium phosphate particles can have both a round shape and a polygonally broken shape that is rounded by wear and thermal sintering.

The aforesaid particles in the size range of 0.1 to 150 μm have pore diameters of 0.01 to 50 μm.

The inventive, plastically deformable preparation can be paste-like or can have a very viscous, more kneadable to wax-like form.

The paste-like form of the preparation is designed such that it can be applied to a bone defect in a minimally invasive manner by means of an injection syringe having a straight or angled cannula.

The diameters of the particles are optimized for the cannula diameter of an injection cannula. Particle diameters are optimized such that the paste-like material can also be applied using an cannula that is angled up to 60°, measured with respect to the longitudinal axis of the injection syringe.

It is essential for the invention that it is constructed from a mixture of 60-90% by mass calcium phosphate particles and 1-30% by mass of an aqueous or alcoholic solution of dextran and/or carboxymethyl dextran and/or hyaluronic acid and/or dermatan sulfate, carboxymethyl cellulose and/or oxidized cellulose and/or gelatins and/or mixtures thereof. The use of polysaccharide derivatives, such as for instance carboxymethyl dextran, carboxymethyl hyaluronic acid, and sulfated hyaluronic acid, is also within the sense of the invention.

It is likewise inventive that it is preferably constructed from a mixture of 80-98% by mass calcium phosphate particles, 1-20% by mass anhydrous polyethylene glycol 400, and 1-20% by mass anhydrous polyethylene glycol 600. Polyethylene glycol 400 and polyethylene glycol 600 can also contain oxidation stabilizers, in addition.

Figure 3:
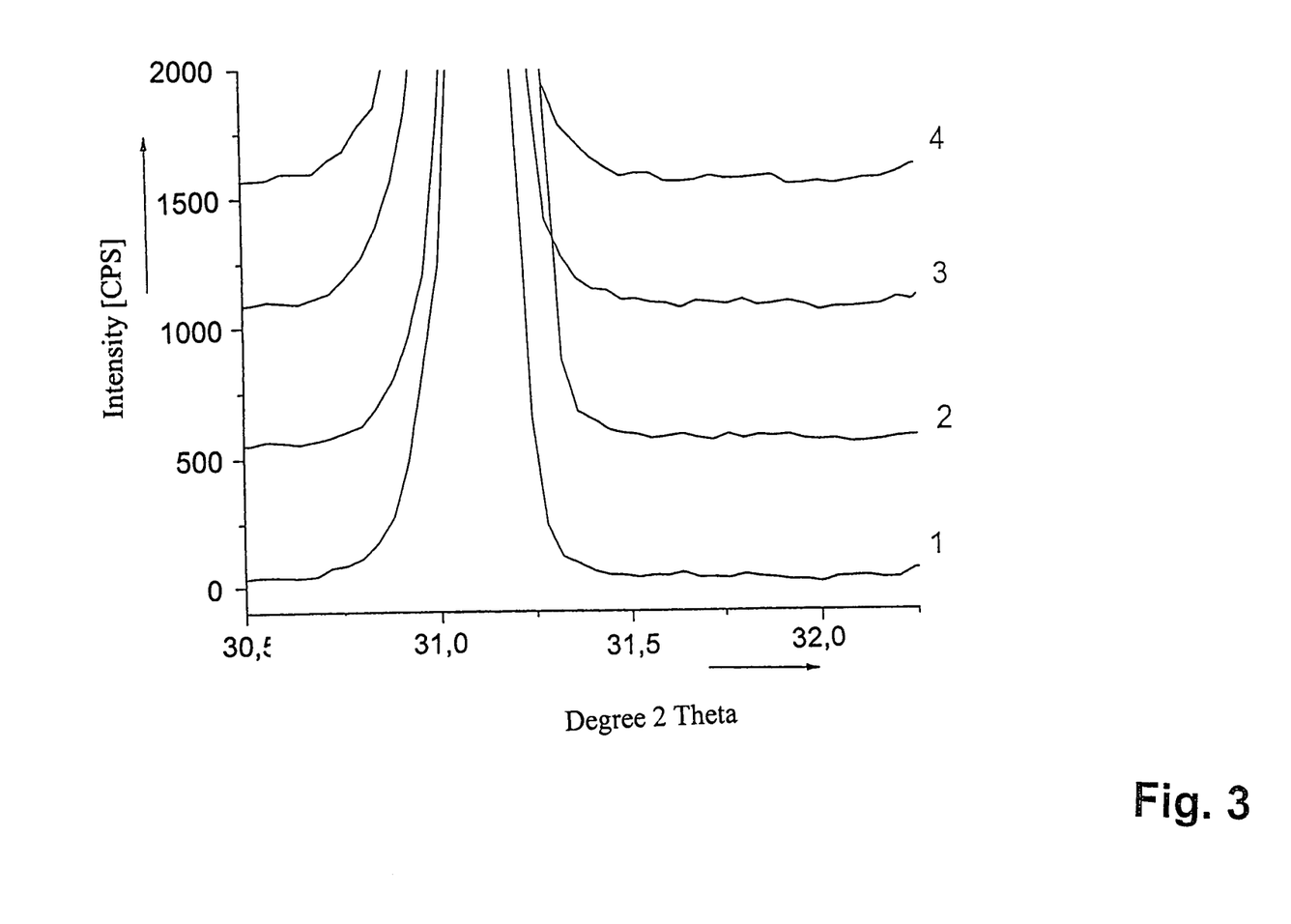
FIG. 3 is a graphic depiction of the measurement results in terms of phase stability of the embodiment of the inventive preparation in accordance with FIG. 1.

FIG. 3 provides detailed images of the x-ray powder diffractograms of
(1) the initial batch of a β-TCP ceramic
(2) β-TCP in hyaluronic acid solution
(3) β-TCP in dextran solution
(4) β-TCP in methylcellulose solution after 12 weeks' storage in water.

As can be seen from this documentation, in the inventive formulation there is no conversion to a different phase of the calcium phosphate family.

Figure 4:
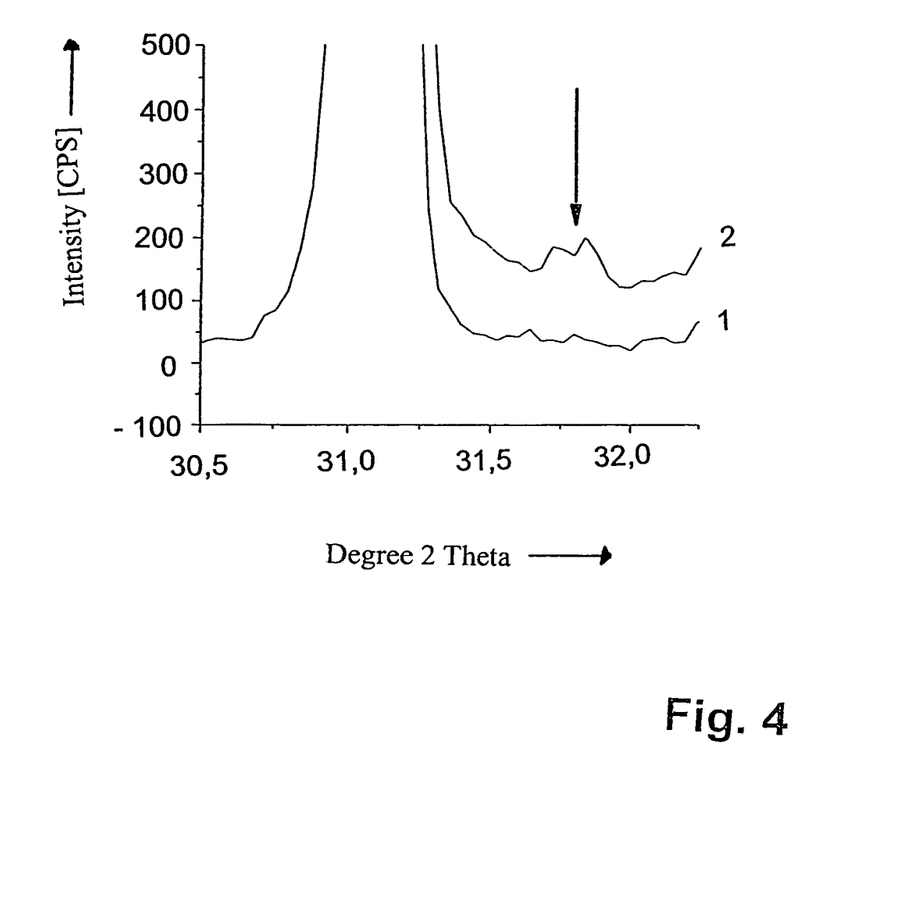
FIG. 4 is another graphic depiction of the measurement results (x-ray powder diffractograms) for the conversion or recrystallization stability of the embodiment of the inventive preparation in accordance with FIG. 1 in various carrying media.
Figure 5:
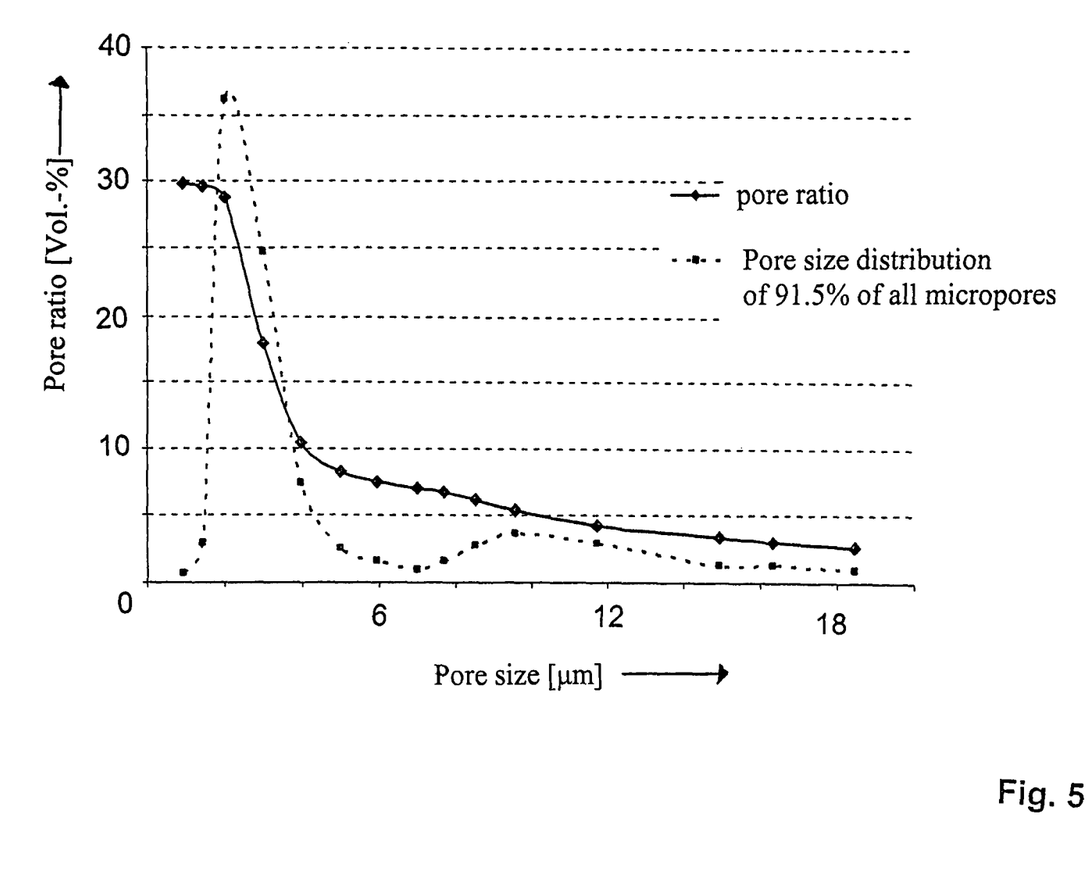
FIG. 5 is a graphic depiction of a mercury pressure porosimetry measurement for determining the pore distribution in the particulate component of the embodiment of the inventive preparation in accordance with FIG. 1, which component is difficult to dissolve.

FIG. 4 provides detailed images of the x-ray powder diffractograms of
(1) the initial batch of a β-TCP ceramic
(2) the same ceramic after 12 weeks' storage in water As can be seen from this documentation, in the aqueous suspension there was partial conversion/recrystallization of β-TCP to hydroxyapatite.

The inventive preparation can be sterilized with dry heat or using gamma rays at a dosage of 8 to 30 kGy (=Kilograys).

The hyaluronic acid used for the inventive preparation or the hyaluronic acid salts can be bioengineered, the hyaluronic acid having a molecular weight of 1,500,000 to 4,500,000 Daltons and sterilization reducing this to 700,000 to 2,500,000 Daltons.

The invention shall be explained using examples in the following, but the invention shall not be limited to these examples.

Components A through K can be used for producing the plastically deformable implant material.

Component A:
Sodium hyaluronate, bioengineered with a molecular weight of 2.5 MDa Component B:
99% β-tricalcium phosphate, free of phase shift, polygonally broken, the broken edges rounded by abrasion and subsequent burning, having a porosity of 20±5% and particle size distribution of 0.1-50 μm, bulk density of 1.1±0.1 g/cm$^3$, and grain size of <63 μm ($d_{50}$=15±5 μm)

Component C:
Warm water for injection (30° C.)

Component D:
Low-viscosity methylcellulose

Component E:
High-viscosity methylcellulose

Component F:
High-viscosity hydroxypropyl cellulose

Component G:
Low-viscosity hydroxypropyl cellulose

Component H:
Polyethylene glycol 400

Component I:
Polyethylene glycol 20,000

Component K:
Dextran

Example 1

0.3 g Component A are added to 20.05 g Component C. After a 4-hour swelling time, the gel is sterile-filtered, slowly added to a total of 50 g Component B, and mixed intimately. The mixture is sterilized in a container at 121° C. using dry heat.

The result is a homogenous mixture with a paste-like consistency that is easily extruded through a cannula, conforms to a defect due to plastic flow, and that air easily hardens superficially, it being possible to accelerate this process using a gentle airflow from a compressed air pistol. After heat sterilization the material has a molecular weight of 1.7±0.5 MDa.

Even after 4 hours of centrifuging, no solid or liquid settles out. An extruded paste adheres well to surrounding tissue. An extruded and superficially dried body retains its shape in the simulated body environment (moist chamber under physiological conditions).

Example 2

0.2 g Component A are added to 20.0 g Component C. After a 4-hour swelling time, the swollen gel is sterile-filtered, slowly added to a total of 63.4 g Component B while stirring, and mixed intimately. The mixture is sterilized in a closed container at 121° C. using dry heat.

The result is a homogenous mixture that has a plastic consistency and is kneadable, that because of its kneadability is easily applied to a bone defect, that adheres well to the surrounding tissue, and that air easily hardens superficially, it being possible to accelerate this process using a gentle airflow from a compressed air pistol. After sterilization the material has a molecular weight of 1.7±0.5 MDa.

Even after 4 hours of centrifuging, no solid or liquid settles out. A hand-formed and superficially dried body retains its shape in the simulated body environment (moist chamber under physiological conditions).

Example 3

225 mg Component D are added to 38 mg Component A, and then 9.7 g Component C is added while stirring. After a 1-hour swelling time, the swollen gel is sterile-filtered, slowly added to a total of 22 g Component B while stirring, and mixed intimately. The mixture is sterilized in a closed container at 121° C. using dry heat.

The result is a homogenous mixture with a paste-like consistency that is easily extruded through a cannula, conforms to a defect due to plastic flow, and that air easily hardens superficially, it being possible to accelerate this process using a gentle airflow from a compressed air pistol. Even after 4 hours of centrifuging, no solid or liquid settles out. A large quantity of the material does not result in an aqueous solution settling on the surface, even after standing for a number of weeks. An extruded paste adheres well to surrounding tissue. An extruded and superficially dried body retains its shape in the simulated body environment (moist chamber under physiological conditions).

Example 4

200 mg Component E are mixed with 100 mg Component A, and then 19 g Component C are added while stirring. After a 1-hour swelling time, the swollen gel is sterile-filtered, slowly added to a total of 58 g Component B while stirring, and mixed intimately. The mixture is sterilized in a closed container at 121° C. using dry heat.

The result is a homogenous mixture that has a plastic consistency and is kneadable, that because of its kneadability is easily applied to a bone defect, that adheres well to the surrounding tissue, and that air easily hardens superficially, it being possible to accelerate this process using a gentle airflow from a compressed air pistol. Even after 4 hours of centrifuging, no solid or liquid settles out. A large quantity of the material does not result in an aqueous solution settling on the surface, even after standing for a number of weeks. A hand-formed and superficially dried body retains its shape in the simulated body environment (moist chamber under physiological conditions).

Example 5

500 mg Component F are mixed with Component C to make 10.0 g. After a 4-hour swelling time, the swollen gel is sterile-filtered, slowly added to a total of 27 g Component B while stirring, and mixed intimately. The mixture is sterilized in a closed container at 121° C. using dry heat.

The result is a homogenous, plastic mass that is kneadable, that because of its kneadability is easily applied to a bone defect, that adheres well to the surrounding tissue, and that air easily hardens superficially, it being possible to accelerate this process using a gentle airflow from a compressed air pistol. Even after 4 hours of centrifuging, no solid or liquid settles out. A hand-formed and superficially dried body retains its shape in the simulated body environment (moist chamber under physiological conditions).

Example 6

500 mg Component G are mixed with Component C to make 10.0 g. After a 4-hour swelling time, the swollen gel is sterile-filtered, slowly added to a total of 22 g Component B while stirring, and mixed intimately. The mixture is sterilized in a closed container at 121° C. using dry heat.

The result is a homogenous, paste-like mixture that is easily extruded through a cannula, conforms to a defect due to plastic flow, and that air easily hardens superficially, it being possible to accelerate this process using a gentle airflow from a compressed air pistol. Even after 4 hours of centrifuging, no solid or liquid settles out. An extruded paste adheres well to surrounding tissue. An extruded and superficially dried body retains its shape in the simulated body environment (moist chamber under physiological conditions).

Example 7

Sterile filtration is performed in 1.9 g Component H. Then 5 g Component B are added slowly while stirring.

The result is a paste that can flow plastically and that is easily extruded through a syringe. The material can easily flow plastically into the intermediate spaces of a defect.

Even after multiple hours of centrifuging, the TCP particles remain in suspension. The material is very suitable for a bone construction material, especially for complicated defects.

Example 8

2.0 g Component I are mixed with Component C to make 10.0 g and after homogenization are sterile filtered. After 25 g Component B are added the material is mixed intensively.

The result is a paste that has good plastic flow and that is easily extruded through a syringe. The material has plastic flow and therefore is ideal for filling intermediate spaces in a defect and adheres to the surrounding tissue.

Even after multiple hours of centrifuging the TCP particles remain in suspension. The material is very suitable for bone construction material, especially for complex defects.

Example 9

0.2 g Component I are mixed with Component H to make 10.0 g and after homogenization are sterile filtered. After 25 g Component B are added the material is mixed intensively.

The result is a non-extrudable, kneadable paste that is slightly elastic and is shapeable like wax. Because of its shapability, the material can be matched well to different defects and remains in the defect temporarily as a placeholder.

Even after multiple hours of centrifuging the TCP particles remain in suspension. The material is very suitable for bone construction material, especially for complex defects.

Example 10

3.0 g Component K are mixed with Component C to make 10.0 g. Once Component K has dissolved, the material is sterile filtered and added to 26.3 g Component B.

The result is a paste that extrudes well through a syringe and that is shapeable and does not drip from the cannula. Because of its shapability, the material can be matched well to different defects and remains temporarily in the defect as a placeholder.

Even after multiple hours of centrifuging the TCP particles remain in suspension. The material is very suitable for bone construction material, especially for minimally-invasive applications.

Example 11

300 g Component D are mixed with Component C to make 10.0 g. After a 1-hour swelling time, 25 g Component B having the mean grain sizes according to the table below are added and mixed intimately. The result is a paste-like mass, the extrudability of which is tested using different cannula diameters.

Extrudability is documented in the table below and indicates the suitability of various particle diameters for producing an extrudable paste.

| Sample | $D_{10}$ [μm] | $D_{50}$ [μm] | $D_{90}$ [μm] | Extrudability through cannula having Ø 0.8 mm | Extrudability through cannula having Ø 2.0 mm |
|---|---|---|---|---|---|
| 1 | 1.60 | 9.65 | 20.28 | ++ | +++ |
| 2 | 2.20 | 15.23 | 35.77 | + | +++ |
| 3 | 10.14 | 27.15 | 44.42 | -- | ++ |
| 4 | 14.89 | 35.52 | 63.60 | --- | + |
| 5 | 19.35 | 44.48 | 78.15 | --- | - |

+++ = very good (good and homogeneous extrudability)
++ = good to very good (good extrudability)
+ = good to moderate (satisfactory extrudability, slight resistance can be detected from canting of individual particles)
- = moderate (adequate extrudability, significant resistance due to canting of particles)
-- = difficult (poor extrudability, particles cant rapidly)
--- = very difficult (not extrudable at all, significant canting).

The advantage of the inventive composition is that a phase and sedimentation-stable, plastically deformable implant material with intrinsic pore formation is provided that can be created such that it does not migrate much and is inserted into a bone defect by injection or alternatively can be applied to/fitted in a bone defect as a kneadable mass.

In the inventive composition, the liquid or paste components that are soluble in water stabilize the biologically active polygonally broken rounded particles that are difficult to dissolve in water and that are in the size range of 0.1-150 μm having pores in the size range of 0.01-50 μm such that they do not convert to other phases or substances due to a dissolution/recrystallization process.

Moreover, with the inventive application of the paste-like implant material/the inventive composition, the water-soluble organic binder substance with the particulate biologically active substance forms a porous structural accumulation that is dimensionally stable when applied, the easily soluble components being exchanged for fibrous tissue in the defect environment so that the porous particle packing remains dimensionally stable and is slowly integrated, vascularized, and resorbed.

All of the features described in the following claims and in the drawings can be essential to the invention, both individually and in any combination with one another.

The invention claimed is:

1. A plastically deformable preparation for bone repair or replacement, comprising a porous particle component that is not easily soluble in water suspended in a paste-like mixture comprising water or alcohol as a solvent and at least one component that is soluble in water or alcohol, the porous particle component that is not easily soluble in water comprising 60-98% by weight and the paste-like mixture comprising 1-30% by weight of the preparation, the particles of the porous particle component having a diameter in a size range that is essentially greater than a phagocytable particle and smaller than the passage diameter of standard injection cannulas and the soluble component comprising 0.1-3% by weight of the preparation, the porous particle component including particle sizes in the range of 0.1 to 50 μm, wherein the component that is soluble in water or alcohol is hyaluronic acid having a molecular weight of 1,500,000 to 4,500,000 Daltons before sterilization of the preparation, and wherein the preparation is sterilizable with dry heat or with gamma rays at a dosage of 8 to 30 kGy.

2. Preparation in accordance with claim 1, wherein the particles of the porous particle component have a polygonally broken shape with a rounded sintered structure.

3. Preparation in accordance with claim 1, wherein the porous particle component that is not easily soluble in water is a biologically active substance.

4. Preparation in accordance with claim 3, wherein the biologically active substance comprises calcium phosphate and/or a bioactive glass ceramic.

5. Preparation in accordance with claim 1, wherein the particles of the porous particle component comprise a calcium phosphate and/or a sodium-containing and/or potassium-containing and/or calcium-containing and/or silicate-containing acid and/or neutral and/or alkaline bioglass or a mixture of the aforesaid.

6. Preparation in accordance with claim 1, wherein the particles of the porous particle component comprise β-tricalcium phosphate containing no other tricalcium phosphate phase.

7. Preparation in accordance with claim 1, wherein the preparation further comprises at least one stabilizing substance that suppresses sedimentation.

8. Preparation in accordance with claim 1, wherein the hyaluronic acid is bioengineered.

9. Preparation in accordance with claim 1, wherein the preparation is administrable through an injection cannula and the particle shape and particle size of the porous particle component are selected based on diameter of the injection cannula so that the preparation can be administered through the injection cannula.

10. Preparation in accordance with claim 1, wherein the preparation is kneadable so that it can be applied to and fitted in a bone defect.

11. Preparation in accordance with claim 1, wherein density of the preparation is 1.3 g/cm$^3$ to 2.1 g/cm$^3$.

12. Preparation in accordance with claim 1, wherein concentration of the component that is soluble in water or alcohol, when dissolved in water or alcohol, is predetermined so that the solution thereof is sufficiently adhesive to connect the particles to form a porous agglomeration that is dimensionally stable when applied.

13. Preparation in accordance with claim 1, wherein the porous particle component is biologically active and comprises a calcium phosphate, or sodium-containing, potassium-containing, calcium-containing or silicate-containing acid or neutral or alkaline bioglass, or a mixture of the aforesaid.

14. Preparation in accordance with claim 1, wherein the porous particle component is biologically active and comprises monocalcium phosphate-monohydrate, anhydrous monocalcium phosphate, dicalcium phosphate-dihydrate, anhydrous dicalcium phosphate, β-tricalcium phosphate, α-tricalcium phosphate, tetracalcium phosphate, whitlockite, octacalcium phosphate, hydroxyapatite, oxyapatite, type A carbonate apatite, type B carbonate apatite, calcium-deficient hydroxyapatite, amorphous calcium phosphate, or amorphous carbonate-containing calcium phosphate, or mixtures of the aforesaid.

15. Preparation in accordance with claim 1, further comprising a growth-inducing protein.

16. Preparation in accordance with claim 1, further comprising a growth factor which is of the growth factor GF family or a bone morphogenetic protein.

17. Preparation in accordance with claim 16, wherein the growth factors are of the group BMP-1 through BMP-12 and/or FGF, TGF-β, PDGF, VEGF, IGF, HGF, PTH, and/or mixtures thereof.

18. A plastically deformable preparation for bone repair or replacement, comprising a porous particle component that is not easily soluble in water suspended in a paste-like mixture comprising water or alcohol as a solvent, platelet rich plasma, and at least one liquid or wax-like component that is soluble in water or alcohol, the porous particle component that is not easily soluble in water comprising 60-98% by weight and the paste-like mixture comprising 1-30% by weight of the preparation, the particles of the porous particle component having a diameter in a size range that is essentially greater than a phagocytable particle and smaller than the passage diameter of standard injection cannulas and the soluble component comprising 0.1-3% by weight of the preparation, the porous particle component including particle sizes in the range of 0.1 to 50 μm, wherein the least one liquid or wax-like component that is soluble in water or alcohol and is dissolved therein is selected from polyethylene glycol 400 and polyethylene glycol 600, the polyethylene glycol 400 and polyethylene glycol 600 containing oxidation stabilizers.

19. Preparation in accordance with claim 11, wherein density of the preparation is 1.6 g/cm$^3$ to 1.9 g/cm$^3$.

20. Preparation in accordance with claim 17, wherein the growth factors are selected from BMP-2 and BMP-7.

21. A method of producing a plastically deformable preparation for bone repair or replacement, comprising a porous particle component that is not easily soluble in water suspended in a paste-like mixture comprising water or alcohol as a solvent and at least one wax-like or gel component that is soluble in water or alcohol, the porous particle component that is not easily soluble in water comprising 60-98% by weight and the paste-like mixture comprising 1-30% by weight of the preparation, the particles of the porous particle component having a diameter in a size range that is essentially greater than a phagocytable particle and smaller than the passage diameter of standard injection cannulas, the soluble component comprising 0.1-3% by weight of the preparation, the porous particle component including particle sizes in the range of 0.1 to 50 μm, the method comprising contacting the wax-like or gel component that is soluble in water or alcohol with water or alcohol as a solvent for a sufficient period, whereby said water or alcohol-soluble component swells, removing excess solvent by filtration under sterile conditions, whereby a hydrogel forms, mixing the hydrogel with the porous particle component for a time sufficient to distribute the particles in the hydrogel, tightly sealing the resultant preparation in a receptacle for applying the preparation, and sterilizing the sealed receptacle containing the preparation by heating for 10-60 min. at 100-130° C.

22. Method of reconstructing a bone, comprising depositing at a defect in the bone a preparation prepared in accordance with claim 1.

23. A plastically deformable preparation for bone repair or replacement, comprising porous β-tricalcium phosphate particles in an amount of 60-80% by weight suspended in a paste-like mixture comprising water in an amount of 17-37% by weight and low-viscosity methylcellulose in an amount of 0.3-3% by weight, the paste-like mixture comprising 1-30% by weight of the preparation, the porous β-tricalcium phosphate particles having a diameter in a size range that is essentially greater than a phagocytable particle and smaller than the passage diameter of standard injection cannulas, the porous β-tricalcium phosphate particles including particle sizes in the range of 0.1 to 50 μm, wherein the preparation is administrable through an injection cannula and the particle shape and particle size of the porous β-tricalcium phosphate particles are selected based on diameter of the injection cannula so that the preparation can be administered through the injection cannula.

24. A plastically deformable preparation for bone repair or replacement, comprising porous β-tricalcium phosphate particles in an amount of 65-85% by weight suspended in a paste-like mixture comprising water in an amount of 13-32% by weight and high-viscosity methylcellulose in an amount of 0.1-3% by weight, the paste-like mixture comprising 1-30% by weight of the preparation, the porous β-tricalcium phosphate particles having a diameter in a size range that is essentially greater than a phagocytable particle and smaller than the passage diameter of standard injection cannulas, the porous β-tricalcium phosphate particles including particle sizes in the range of 0.1 to 50 μm.

25. A plastically deformable preparation for bone repair or replacement, comprising porous β-tricalcium phosphate particles in an amount of 60-80% by weight suspended in a paste-like mixture comprising water in an amount of 15-35% by weight, low-viscosity methylcellulose in an amount of 0.1-3% by weight and sodium hyaluronate or hyaluronic acid in an amount of 0.01-2% by weight, the paste-like mixture comprising 1-30% by weight of the preparation, the porous β-tricalcium phosphate particles having a diameter in a size range that is essentially greater than a phagocytable particle and smaller than the passage diameter of standard injection cannulas, the porous β-tricalcium phosphate particles including particle sizes in the range of 0.1 to 50 μm.

26. A plastically deformable preparation for bone repair or replacement, comprising porous calcium phosphate particles in an amount of 20-98% by mass suspended in a paste-like mixture comprising water or alcohol and components that are soluble in water or alcohol and form a hydrogel therein, the soluble hydrogel-forming components comprising, prior to combining with water or alcohol, 1-20% by mass anhydrous polyethylene glycol 400 and 1-20% by mass anhydrous polyethylene glycol 600, the paste-like mixture comprising 1-30% by weight of the preparation, the porous calcium phosphate particles having a diameter in a size range that is essentially greater than a phagocytable particle and smaller than the passage diameter of standard injection cannulas, the porous β-tricalcium phosphate particles including particle sizes in the range of 0.1 to 50 μm, and the percentage in mass of the preparation components not exceeding 100%.

27. Preparation in accordance with claim 23, comprising a mixture of 67-75% by weight β-tricalcium phosphate, 25-35% by weight water and 0.5-1.5% by weight low-viscosity methylcellulose.

28. Preparation in accordance with claim 24, comprising a mixture of 68-78% by weight β-tricalcium phosphate, 13-32% by weight water and 0.3-1.0% by weight high-viscosity methylcellulose.

29. Preparation in accordance with claim 25, comprising a mixture of 68-76% by weight β-tricalcium phosphate, 25-31% by weight water, 0.2-0.9% by weight low-viscosity methylcellulose, and 0.1-0.6% by weight sodium hyaluronate or hyaluronic acid.

30. A method of producing the plastically deformable preparation for bone repair or replacement of claim 26, the method comprising suspending the porous calcium phosphate particles in an amount of 20-98% by mass in the paste-like mixture comprising water or alcohol and polyethylene glycol 400 in an amount of 1-20% by mass and polyethylene glycol 600 in an amount of 1-20% by mass to form a mixture of the particulate component in the paste-like mixture, the polyethylene glycol 400 and the polyethylene glycol 400 being anhydrous prior to the suspending, the paste-like mixture comprising 1-30% by weight of the preparation, the porous calcium phosphate particles having a diameter in a size range that is essentially greater than a phagocytable particle and smaller than the passage diameter of standard injection cannulas, the porous β-tricalcium phosphate particles including particle sizes in the range of 0.1 to 50 μm, and the percentage in mass of the preparation components not exceeding 100%.

31. Method according to claim 30 or 21, further comprising adding a stabilizing substance that suppresses sedimentation.

* * * * *